(12) United States Patent
Blocher et al.

(10) Patent No.: US 8,568,442 B2
(45) Date of Patent: Oct. 29, 2013

(54) MEDICAL GRIPPING AND/OR CUTTING INSTRUMENT

(75) Inventors: Martin Blocher, Tuttlingen (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1674 days.

(21) Appl. No.: 11/452,740

(22) Filed: Jun. 14, 2006

(65) Prior Publication Data
US 2009/0082795 A1    Mar. 26, 2009

(30) Foreign Application Priority Data

Jun. 14, 2005 (DE) .......................... 10 2005 027 419

(51) Int. Cl.
*A61B 17/00* (2006.01)

(52) U.S. Cl.
USPC ..................................... 606/205; 606/208

(58) Field of Classification Search
USPC ................... 606/206–208, 210, 211, 209; 81/318–325, 328, 337–340, 345, 391, 81/392, 405–414
See application file for complete search history.

(56) References Cited

U.S. PATENT DOCUMENTS

| | | | | |
|---|---|---|---|---|
| 1,189,561 A | * | 7/1916 | Griminger | 81/320 |
| 4,189,839 A | * | 2/1980 | Manuel | 433/4 |
| 5,584,844 A | * | 12/1996 | Weisshaupt | 606/170 |
| 5,951,587 A | | 9/1999 | Qureshi et al. | 606/207 |
| 6,832,532 B2 | * | 12/2004 | Kilpela et al. | 81/315 |
| 7,464,846 B2 | * | 12/2008 | Shelton et al. | 227/175.1 |
| 2004/0158233 A1 | * | 8/2004 | DiCesare et al. | 606/1 |
| 2004/0167569 A1 | * | 8/2004 | Dicesare et al. | 606/208 |

FOREIGN PATENT DOCUMENTS

DE    273689    8/1913

OTHER PUBLICATIONS

German Office Action, Mar. 10, 2006, 4 pages.

\* cited by examiner

*Primary Examiner* — Thomas McEvoy
(74) *Attorney, Agent, or Firm* — St. Onge Steward Johnston & Reens LLC

(57) ABSTRACT

The invention relates to a medical gripping and/or cutting instrument having a shaft on whose distal end a tool is positioned consisting of at least two jaw members and on whose proximal end a handle is positioned consisting of at least two gripping members. For opening and closing, at least one jaw member of the tool can move by means of a rotatably configured gripping member of the handle with respect to the other jaw member of the tool, and the rotatable gripping member of the handle can be secured by means of a notching mechanism on the at least one other gripping member of the handle, with the jaw members in an at least partly closed position. To produce a medical gripping and/or cutting instrument which allows a simple and rapid unnotching of the gripping members of the handle, it is proposed with the invention that a portion of at least one gripping member of the handle can move with respect to the remaining portion of this gripping member in such a way that the notching mechanism can be released, with the gripping members in an essentially unchanged position with respect to one another.

7 Claims, 5 Drawing Sheets

MEDICAL GRIPPING AND/OR CUTTING INSTRUMENT

CROSS-REFERENCE TO RELATED APPLICATIONS

The present application claims priority of German patent application No. 10 2005 027 419.6 filed on Jun. 14, 2005, the content of which is incorporated herein by reference.

FIELD OF THE INVENTION

The invention relates to a gripping and/or cutting instrument having a shaft on whose distal end a tool is positioned consisting of at least two jaw members and on whose proximal end a handle is positioned consisting of at least two gripping members. For opening and closing, at least one jaw member of the tool can be displaced with respect to the other jaw member of the tool by means of a gripping member of the handle configured so that it can rotate, and the rotatable gripping member of the handle can be secured by means of a notching mechanism onto the at least one other gripping member of the handle, with the jaw members in an at least partly closed position.

BACKGROUND OF THE INVENTION

Generic medical instruments are known in the art in various embodiments. The notching of the gripping members of the handle in the closed position of the jaw members is advantageous, for instance, in the configuration of the instrument as a needle holder, because in this manner a needle gripped by the jaw members remains securely between the jaw members even without the operator constantly pressing the gripping members together. The disadvantage with known medical instruments is that the gripping members must be released or gripped anew in a different manner for unnotching.

It is consequently the object of the invention to create a medical gripping and/or cutting instrument that allows an easy and rapid unnotching of the gripping members of the handle.

SUMMARY OF THE INVENTION

This aim is realized by means of the invention in such a manner that a portion of at least one gripping member of the handle can be moved with respect to the remaining portion of this gripping member in such a way that the notching mechanism can be released with the gripping members in an essentially unchanged position with respect to one another.

Thanks to the invention's configuration of a portion of a handle to be movable with respect to the rest of the gripping member, it is possible for the first time to release the notching of the gripping members again without releasing or changing the grip and with the position of the gripping members to one another unchanged or at least essentially unchanged.

According to a practical embodiment of the invention, it is proposed that the movable portion of the gripping member is mounted on the remaining rigid portion of this gripping member so that it can be displaced by rectilinear and/or rotary motion, so that it requires only a pushing and/or twisting of this specially configured portion of the handle in order to unlock the notching mechanism.

The notching mechanism of this invention, according to a preferred embodiment, consists of a notching hook which is mounted so that it can pivot on a gripping member and which can be secured in a notching recess on the other gripping member and can be released from its notching position in the notching recess by displacing the movable portion of the gripping member.

It is further proposed with the invention that in order to configure the notching recess the recess is configured as a serration, which is shaped to match a rigid stud extending from the particular gripping member.

It is proposed with a preferred embodiment of the invention that the movable portion of the gripping member is configured as a gripping area that can slide rectilinearly against the force of a pressure spring. The pressure spring ensures that the movable portion of the gripping member is returned again to the starting position after release of the notching. In addition, the pressure spring prevents accidental pushing of the movable portion and thus an accidental opening of the notching, because the pressure spring forms a counter force against the pushing of the movable portion.

To limit the travel path of the movable portion of the gripping member, the gripping member has two stops, between which the movable portion can be slid. The movable portion of the gripping member is mounted on the rigid portion of the same gripping member, according to the invention, by linked undercuttings on the two portions of the gripping member.

It is further proposed with the invention that the notching hook is mounted so that it can pivot on the rigid portion of the gripping member and interacts with the movable portion of the gripping member by means of a guide pin, so that the guide pin is preferably shaped to match the notching hook, on the one hand, and with its free end engages in a guide recess in the movable portion of the gripping member.

Displacement of the notching hook can be facilitated, according to the invention, if a gliding element, in particular a roller, is formed to match the free end of the guide recess that is mounted in the guide recess.

According to an additional embodiment of the invention, the notching of the notching mechanism can be further reinforced if the notching hook is pretensioned by means of a spring element in the direction toward the notching position.

It is finally proposed with the invention that the gripping members of the handle are pretensioned in the open position by means of a spring element. This tensioning of the gripping members serves, first, to reinforce the notching by the notching mechanism in the notched position, because the tensioning intensifies the engagement of the notching hook in the serration and, second, in the opened notching mechanism, the tensioning serves to move the gripping members of the handle into the opened position without any action by the operator.

Further characteristics and advantages of the invention can be seen from the annexed illustrations, in which an embodiment of a medical gripping and/or cutting instrument according to this invention is depicted in merely exemplary form.

DETAILED DESCRIPTION OF THE INVENTION

Figure 1:
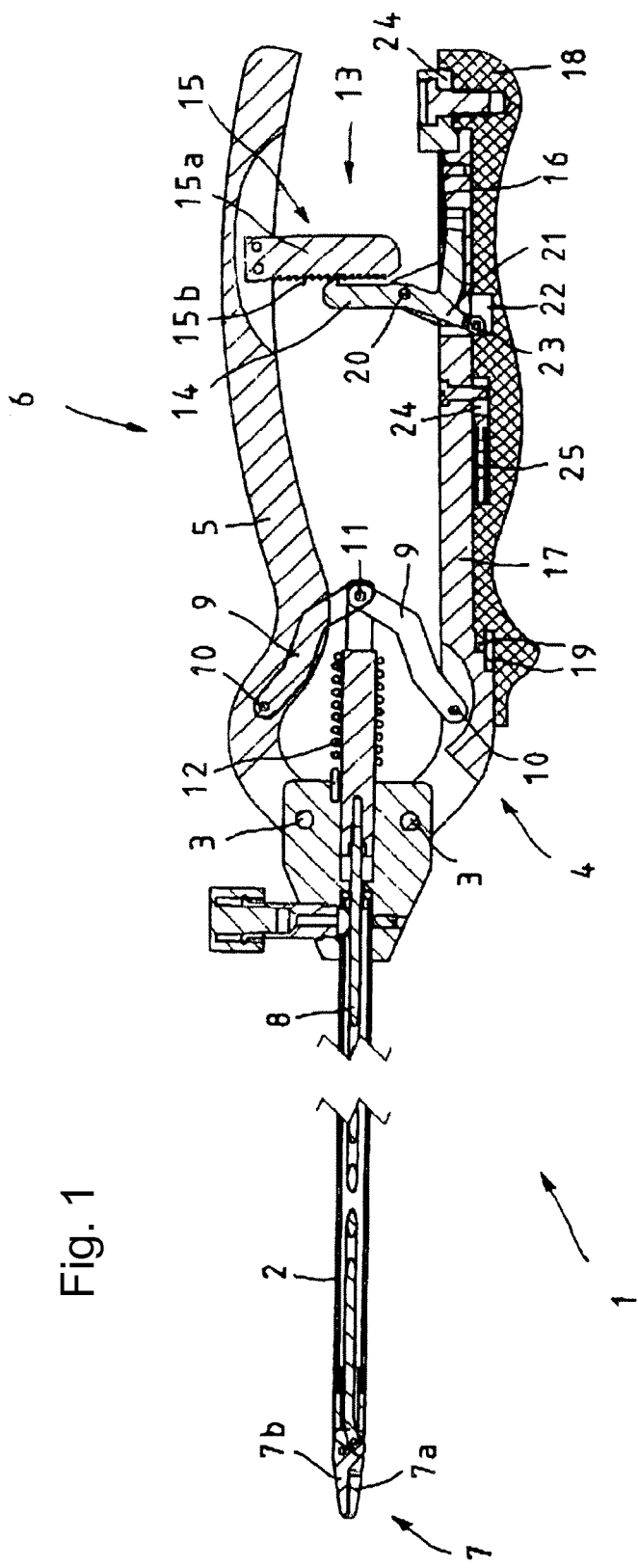
FIG. 1 shows a longitudinal section through a medical gripping and/or cutting instrument according to the invention, showing the gripping members of the handle in the notched stopped position.
Figure 2:
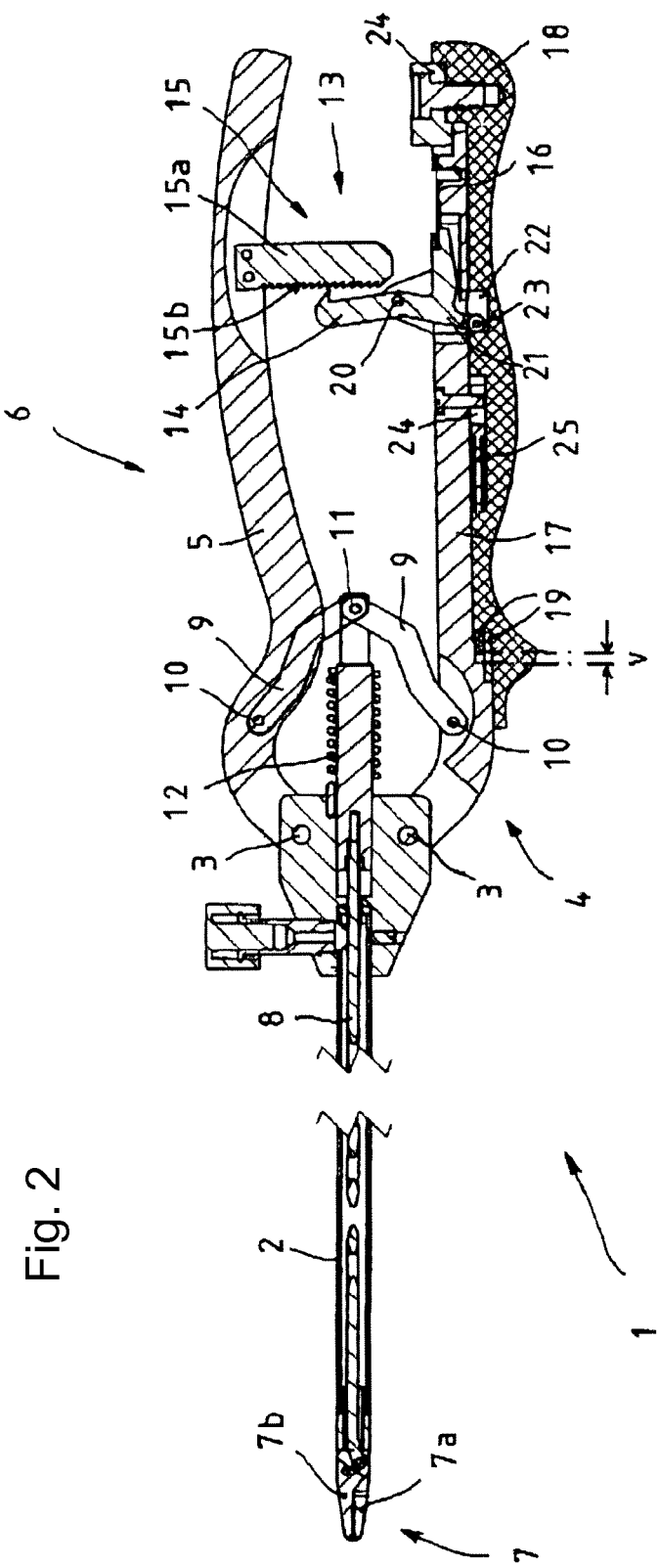
FIG. 2 shows a view, according to FIG. 1, but with opened notching mechanism.
Figure 3:
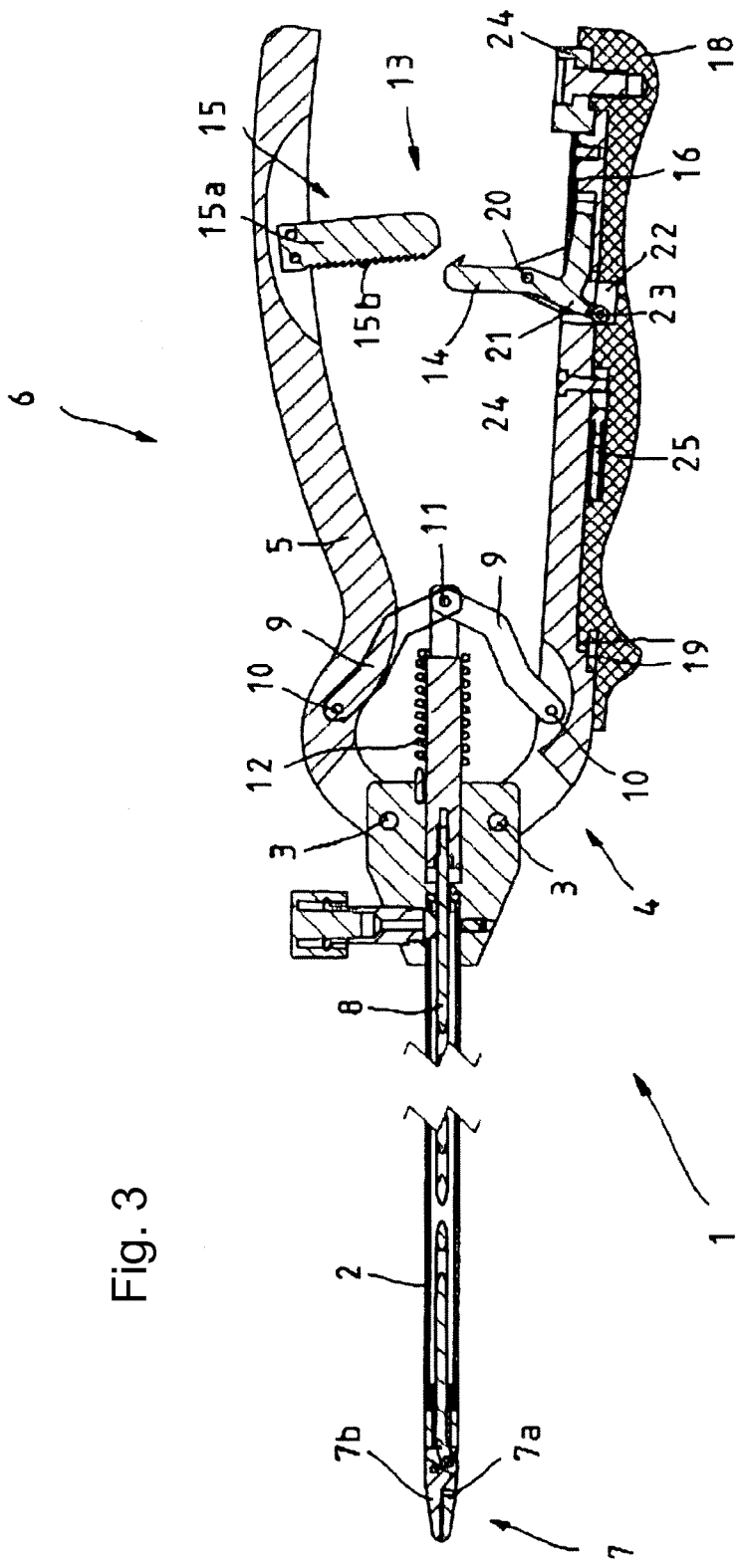
FIG. 3 shows a longitudinal section through a medical gripping and/or cutting instrument according to FIGS. 1 and 2, showing the gripping members of the handle in the opened position.

The drawings in FIGS. 1 to 3 show lateral sectional views of a medical gripping and/or cutting instrument 1, whose power transmission mechanism can be used in a variety of ways, for instance as punches, scissors, needle holders, gripping instruments, and the like.

The illustrated medical instrument 1 consists essentially of a hollow shaft 2 having on its proximal end a handle 6 consisting of two gripping members 4 and 5 that can rotate in each case around a related axis of rotation 3. On the distal end of the shaft 2 there is a tool 7 positioned, which consists of a jaw member 7a connected rigidly with the shaft 2 and a rotatable jaw member 7b. For opening and closing the jaw members 7a and 7b of the tool 7 by means of the activation of the rotatable gripping members 4 and 5 of the handle 6, the gripping members 4, 5 and the rotatable jaw member 7b are actively connected with one another by means of a push-pull rod 8.

As can be seen from FIGS. 1 to 3, the gripping members 4 and 5 are coupled with the push-pull rod 8 in the illustrated embodiment by means of interposed pivot levers 9, which are mounted rotatably with one free end on a support point 10 on one of the gripping members 4, 5 and with the other fee end on a common axis of rotation 11 on the push-pull rod 8. The linking of the gripping members 4 and 5 with the push-pull rod 8 by means of the pivot levers 9 is arranged in such a way that upon pressing the gripping members 4, 5 together, the push-pull rod 8 is pulled by the pivot levers 9 to the proximal end of the medical instrument 1, in turn causing the rotatable jaw member 7b of the tool 7 to rotate into the closed position.

To open the jaw members 7a, 7b of the tool 7 thus requires the spreading motion of the gripping members 4, 5 of the handle 6, so that the push-pull rod 8 is pressed by the pivot gears 9 to the distal end of the medical instrument. To facilitate the pushing apart of the gripping members 4, 5 of the handle 6, a spring element 12 in the form of a draw spring is positioned on the push-pull rod 8 and causes the gripping members 4, 5 to be pretensioned into the open position.

To secure the jaw members 7a, 7b of the tool 7 in the closed or at least partially closed position, which is advantageous for instance in configuring the medical instrument as a needle holder, the handle 6 has a notching mechanism 3 by which the gripping members 4 and 5 can be secured with respect to one another. As soon as the gripping members 4, 5 are secured in place by the notching mechanism 1, the operator can hold the handle 6 without permanently pressuring the gripping members 4, 5, without running the risk of losing a part that is grasped by the tool 7, for instance a surgical needle.

In the illustrated embodiment the notching mechanism 13 consists of a notching hook 14 mounted rotatably on the gripping member 4 and a notching recess 15 formed on the gripping member 5, which in turn consists of a rigid stud 15a extending essentially perpendicularly from the gripping member 5 and a serration 15b on the stud 15a serving for the insertion of the notching hook 14. To reinforce the engagement of the notching hook 14 into the serration 15b of the notching recess 15, the notching hook in the illustrated embodiment is pretensioned in the notched position by a spring element 16 preferably taking the form of a leaf spring.

In order to unlock the notching mechanism 13 without releasing the gripping members 4, 5, which makes it a lot easier for an operator to use, the gripping member 4 has a bipartite construction. Specifically, the gripping member 4 includes a rigid portion 17 and a movable portion 18 that can move with respect to the rigid portion 17. In the illustrated embodiment, the movable portion 18 is positioned on the rigid portion 17 of the gripping member 4, such that it can move in a linear direction. The portions 17 and 18 are positioned on one another by means of undercuttings 19 on the respective portions 17 and 18 that connect together.

In addition to the illustrated purely rectilinear displacement of the movable portions 8 of the gripping member 4, it is also possible of course to conduct the displacement in purely rotary or combined rectilinear and rotary form.

Figure 4:
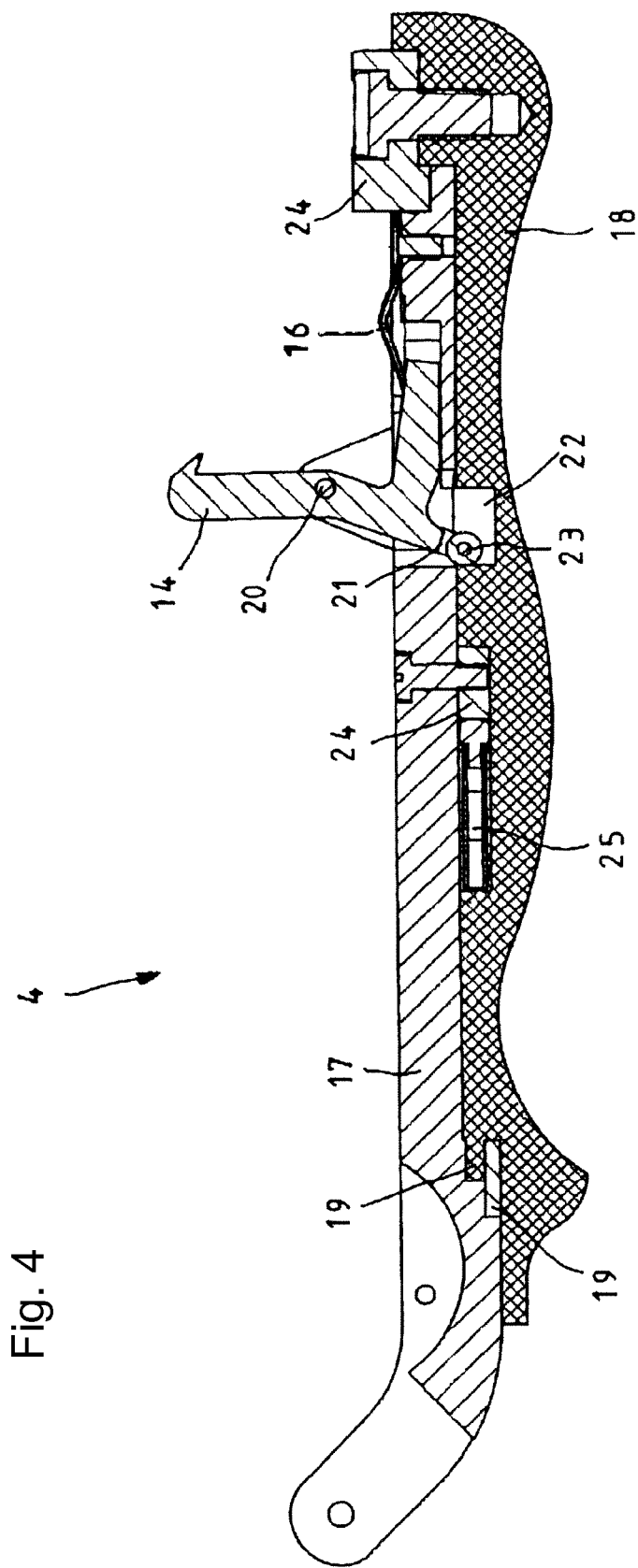
FIG. 4 shows an enlarged view of the lower gripping member of the handle according to FIGS. 1 and 3.
Figure 5:
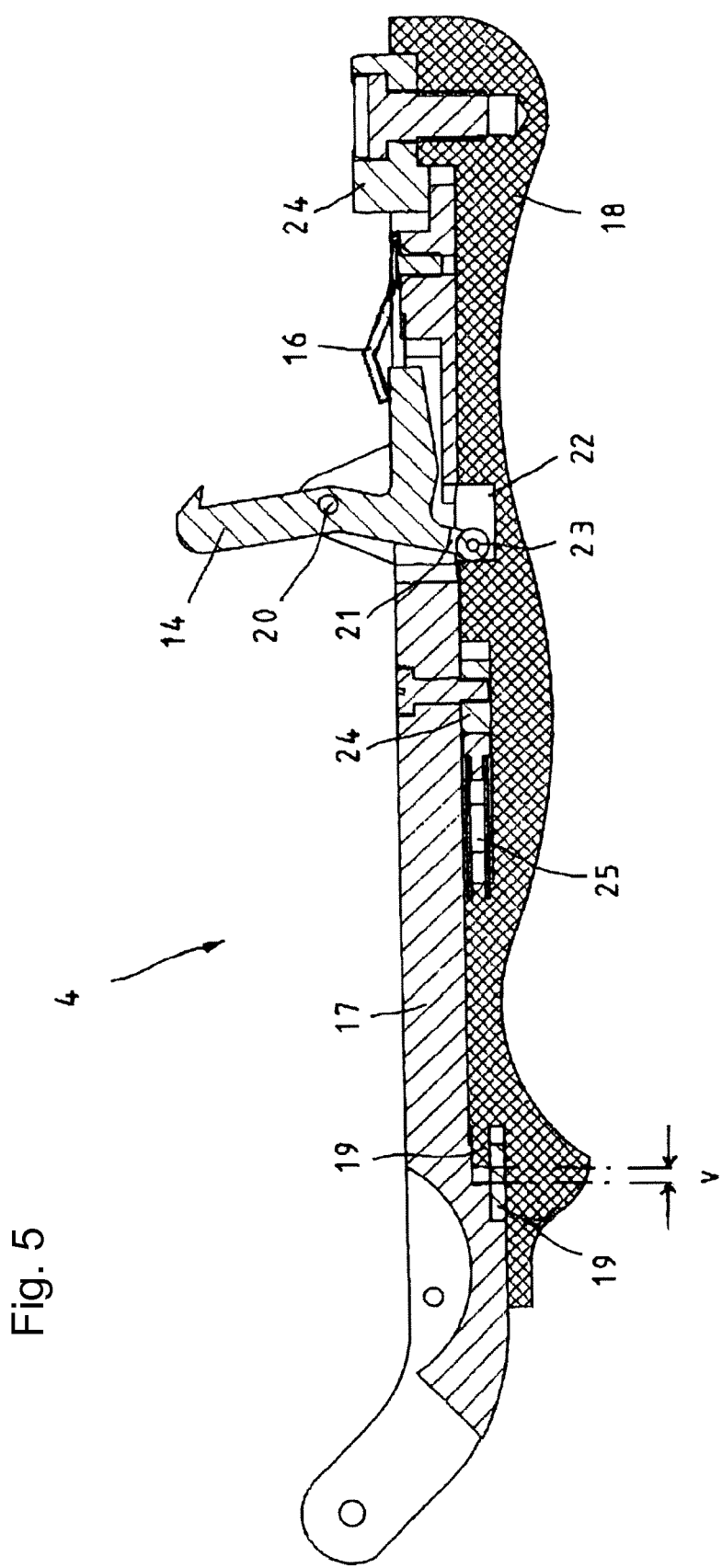
FIG. 5 shows an enlarged view of the lower gripping member of the handle according to FIG. 2.

The construction of the gripping member 4 consisting of the two portions 17 and 18 can be seen in particular from the enlarged detail views of the gripping member 4 according to FIGS. 4 and 5.

The actual unlocking of the notching mechanism 13 by the movable portion 18 of the gripping member 4 occurs in such a way that the notching hook 14 can be brought out of engagement with the notching recess 15 by displacing the adjustable portion 18. For this purpose the notching hook 14 is mounted so that it can rotate around an axis 20 on the rigid portion 17 of the gripping member 4 and has a shaped guide pin 21, which engages in a guide pocket 22 configured in the adjustable portion of the gripping member 4. Then, as soon as the displaceable portion 8 of the gripping member 4 is pushed, this pushing necessarily drags with it the guide pin 21 of the notching hook 14, which is mounted in the guide pocket 22, which hook is rotated in this motion around the axis 20. To facilitate displacement of the notching hook 14, a gliding element taking the form of a roller 23 is mounted on the free end of the guide pin 21 mounted in the guide pocket 22.

To restrict a pathway v, as it is represented in FIGS. 2 and 5, that can be traversed by the movable portion 18 of the gripping member 4, two stops 24 are provided, in such a way that in the illustrated embodiment the stop 24 on the distal side is firmly connected with the rigid portion 17 of the gripping member 4 and the proximal stop 24 is firmly connected with the movable portion 18 of the gripping member 4.

As can further be seen, in particular from FIGS. 4 and 5, in the movable portion 18 of the gripping member 4 there is a spring element 25, preferably a draw spring, abutting the stop 24 of the rigid portion 17 of the gripping member 4, and by means of this spring element the movable portion 18 of the gripping member 4 is pretensioned in the notched position.

Operation of the medical instrument 1 described above and illustrated in FIGS. 1 to 3 proceeds as follows:

Beginning from the start position shown in FIG. 3, in which both the jaw members 7a, 7b of the tool 7 and the gripping members 4 and 5 of the handle 6 are opened, the operator grasps the medical instrument 1 in order to grip and hold, for instance, a surgical needle by means of the tool 7. For this purpose the operator presses together the gripping members 4 and 5 of the handle 6, which he holds with one hand, until they have assumed, for instance, the position shown in FIG. 1.

Because of the coupling of the gripping members 4, 5 with the push-pull rod 8 by the pivot levers 9, the pressing together of the gripping members 4 and 5 causes the rotatable jaw member 7b to pivot and thus leads to the closing of the tool 7.

Upon pressing together the gripping members 4 and 5, the notching hook 14 and the notching recess 15 of the notching mechanism 13 approach closer to one another in such a way that the notching hook 14 is pretensioned by the spring element 16 in the notching position, notching automatically, and engages in the serration 15b of the notching recess 15 and thus fixes the handles 4 and 5 with respect to one another. This fixing of the gripping members 4 and 5 causes at the same time a fixing of the jaw members 7a and 7b of the tool 7. In this position illustrated in FIG. 1 the surgical needle, for instance, that is gripped by the tool 7 is held reliably and firmly in place, without the operator needing to press together the gripping members 4 and 5 for an extended period.

If the operator then wishes to release the notching of the gripping members 7 and 5 again by means of the notching mechanism 13, he needs merely to shove the movable portion 18 of the gripping member 4 backward against the rebounding force of the spring element 25 with the fingers he is using to hold this gripping member. Thanks to the coupling of the notching hook 14 with the movable portion 18 of the gripping member 4, by the guide pin 21 mounted in the guide pocket 22, this pushing of the movable portion 18 of the gripping member 4 causes the notching hook 14 to go out of engagement with the notching recess 15, as shown in FIG. 2. The corresponding position of the movable portion 18 to the rigid portion 17 of the gripping member 4 can be seen with particular clarity in FIG. 5.

The spring element 12 mounted on the push-pull rod 8, which serves to pretension the gripping members 4 and 5 of the handle 6 in the open position, ensures then that the gripping members 4 and 5 of the handle 6 are pressed apart again into the open position shown in FIG. 3.

A medical instrument 1 configured in this way is distinguished in that the notching mechanism 13 that fixes the gripping members 4 and 5 of the handle 6 against one another can be opened again without releasing the gripping members 4, 5.

What is claimed is:

1. A medical gripping and/or cutting instrument having a shaft on whose distal end is a tool comprising at least two jaw members and on whose proximal end is a handle comprising at least two gripping members, wherein for opening and closing, one of the gripping members is rotatably configured such that at least one jaw member of the tool can move with respect to the other jaw member of the tool, wherein the at least one movable jaw member and the rotatable gripping member are actively connected with one another via a push-pull rod, wherein the instrument comprises a notching mechanism and wherein the rotatable gripping member of the handle can be secured to at least one other of the at least two gripping members of the handle by the notching mechanism, with the jaw members in an at least partly closed position, wherein one gripping member of the handle consists of two portions, namely a rigid portion and a movable portion, wherein the movable portion and the rigid portion of said one gripping member are positioned on one another by linked undercuttings on the rigid portion and the movable portion of said one gripping member that connect together so that, with one hand only, the movable portion can be held and moved in the longitudinal direction of said one gripping member with respect to the rigid portion of said one gripping member in such a way that the notching mechanism can be released without essentially changing the position of the at least two gripping members to one another;

wherein the notching mechanism comprises a guide pin and a notching hook rotatably positioned on the rigid portion of said one gripping member such that it can pivot and interact with the movable portion of said one gripping member via the guide pin, wherein the notching mechanism further comprises a notching recess on another of the at least two gripping members such that the notching hook can be secured in the notching recess;

wherein the guide pin engages in a guide pocket in the movable portion of said one gripping member; and wherein a free end of the guide pin is positioned in the guide pocket and has a gliding element, in particular a roller.

2. The medical gripping and/or cutting instrument according to claim 1, wherein the notching recess is configured as a serration, which is shaped on a rigid stud extending from the another gripping member.

3. The medical gripping and/or cutting instrument according to claim 1, wherein the notching hook can be released from a notched position in the notching recess by displacement of the movable portion of said one gripping member.

4. The medical gripping and/or cutting instrument according to claim 1, wherein the movable portion of said one gripping member is configured as a gripping area that can slide rectilinearly against the force of a pressure spring.

5. The medical gripping and/or cutting instrument according to claim 4, wherein said one gripping member has two stops, and wherein the movable portion of said one gripping member can be slid between the two stops that restrict the travel path.

6. The medical gripping and/or cutting instrument according to claim 1, wherein the notching hook is pretensioned by a spring element in a direction toward a notching position.

7. The medical gripping and/or cutting instrument according to claim 1, wherein the at least two gripping members of the handle are pretensioned by a spring element in an open position.

* * * * *